United States Patent [19]

Weber

[11] 4,307,473

[45] Dec. 29, 1981

[54] PROSTHETIC WRIST JOINT

[76] Inventor: Edward R. Weber, 13717 Rivercrest Dr., Little Rock, Ark. 72211

[21] Appl. No.: 120,559

[22] Filed: Feb. 11, 1980

[51] Int. Cl.³ .............................................. A61F 1/03
[52] U.S. Cl. .................................... 3/1.91; 128/92 C
[58] Field of Search ............................. 3/1.91, 1.911; 128/92 C

[56] References Cited

U.S. PATENT DOCUMENTS

| | | | |
|---|---|---|---|
| 3,506,982 | 4/1970 | Steffee | 3/1.91 |
| 3,813,700 | 6/1974 | Tavernetti et al. | 3/1.91 |
| 3,816,854 | 6/1974 | Schlein | 3/1.91 |
| 3,934,272 | 1/1976 | Wearne et al. | 3/1.911 |
| 3,991,425 | 11/1976 | Martin et al. | 3/1.91 |
| 4,003,096 | 1/1977 | Frey | 3/1.91 |
| 4,040,130 | 8/1977 | Lavre | 3/1.91 |
| 4,063,314 | 12/1977 | Loda | 3/1.91 |
| 4,106,128 | 8/1978 | Greenwald et al. | 3/1.91 |
| 4,131,965 | 1/1979 | Treace | 3/1.91 |
| 4,180,871 | 1/1980 | Hamas | 3/1.91 |
| 4,259,752 | 4/1981 | Taleisnik | 3/1.91 |

*Primary Examiner*—Clifford D. Crowder
*Attorney, Agent, or Firm*—Roberts and Stout

[57] ABSTRACT

A prosthetic wrist joint for anchoring into the radius and the metacarpals includes a radial component, a metacarpal component and an intermediate component. The radial component has a part-cylindrical bearing surface and a stem portion for insertion into the end of the radius bone. The metacarpal component has a ball-like hinge portion and a pair of outwardly protruding prongs for anchoring into the second metacarpal and the third metacarpal. The intermediate component includes a cylindrical bearing surface which cooperatively engages the part-cylindrical bearing surface of the radial component, and a socket-like recess for receiving the ball-like hinge portion of the metacarpal component for movement in the direction of radial-ulnar deviation. The modified ball and socket arrangement between the metacarpal component and the intermediate component permit limited rotational movement about the longitudinal axis of the arm. The three components are arranged such as to have a full range of motion wherein wrist motion is limited solely by the surrounding soft tissue rather than by the wrist prosthesis components. The calculated rotational motion has an axis which is coincident with the anatomical center of rotation of the wrist rather than being centered about the stem axis of the prosthesis. The intermediate component is arranged relative to the radial component such that when the prosthetic wrist joint is loaded beyond its capacity in one of the various motion planes, the intermediate component will dislocate rather than break or loosen.

16 Claims, 9 Drawing Figures

PROSTHETIC WRIST JOINT

BACKGROUND OF THE INVENTION

This invention relates in general to endoprosthetic devices and in particular to endoprosthetic wrist joints.

Wrist joints are commonly susceptible to fracture, rheumatic infection and metacarpal-radial arthritis, any one of which can severally affect the ability of the wrist to perform its major functions of flexion, extension and rotation. What complicates the design of a suitable prosthetic replacement for an infected or damaged wrist portion is the complex osteoarthromuscular structure of the wrist and the heavy pressures to which a wrist is subjected during normal use.

A preferred endoprosthetic wrist joint is one which permits a full range of motion in every plane except rotational and includes a biomechanically (anatomical) accurate center of rotation. A full range of motion is one which is limited solely by the surrounding soft tissue of the anatomy rather than by the prosthesis structure. Anatomically centered means that the center of rotation is with respect to the anatomy of the wrist and not with respect to the stem axis of the prosthesis. Studies have shown that the anatomical center of rotation in the wrist is in the head of the capitate bone (ulnarward) and displaced slightly volarward. Providing a prosthesis with an anatomical center is important in that it permits restoration of an arthritic hand to its normal position. Patients with severe metacarpal-radial arthritis have hands which are pulled ulnarward and volarward. The reason for the arthritic deformity is that the deteriorated wrist has reduced the leverage of the dorsal and radial muscles in the hand. By using a prosthesis with an anatomical center, the dorsal and radial muscles regain their correct positioning and leverage and draw the hand back into a normal position.

A further consideration in the design of a suitable wrist prosthesis is the amount of motion in the rotational plane which is to be permitted, if any. Some wrist prostheses are arranged to prevent rotational movement. The calculated amount of rotation included in this design, however, does allow for small rotational displacements of the metacarpals with respect to the radius and this rotational displacement obviates stress being absorbed by one of the structural components of the prosthesis. This torque relief discourages cement loosening of the implanted component at the cement-to-bone interface. A still further design consideration is to allow the components of the prosthesis to dislocate from each other when loaded beyond capacity rather than break or loosen. Thus, such a prosthesis is able to be relocated by closed reduction which spares the patient the significant pain involved in reoperating to repair a broken or loosened prosthesis.

The following listed patents provide some indication of prosthetic wrist joints which have been conceived; however, none of these joints provide the various desirable features which have been mentioned above.

| U.S. Pat. No. | Patentee | Issue Date |
|---|---|---|
| 2,220,235 | Langlais (French) | 4/10/74 |
| 3,506,982 | Steffee | 4/21/70 |
| 3,837,008 | Bahler et al. | 9/24/74 |
| 3,909,853 | Lennox | 10/07/75 |
| 4,003,096 | Frey | 1/18/77 |
| 4,040,130 | Laure | 8/09/77 |
| 4,063,314 | Loda | 12/20/77 |
| 4,100,626 | White | 7/18/78 |
| 4,180,871 | Hamas | 1/01/80 |

Langlais discloses a three-component prosthetic joint wherein motion in one plane is limited to the interface between the first and second components and motion in a different plane is limited to the interface between the second and third components. No rotational movement is permitted and the extent of movement in the first two planes is limited by the sides of the first and second components, respectively.

Steffee discloses an endoprosthetic joint wherein a modified ball and socket combination is employed. The socket opening is shaped so as to determine the limits of flexion, extension, hyperextension, adduction and abduction which the prosthesis shall be capable of approximating in usage. A key and keyway arrangement are provided to eliminate rotation about the longitudinal axis of the prosthesis.

Bahler et al. discloses an endoprosthetic wrist joint of a modified ball and socket combination. The generally spherical ball includes a radially protruding portion which is perpendicular to the longitudinal axis of the forearm and the generally spherical socket is provided with a slit-like guide to receive the protuding portion and prevent rotation about the longitudinal axis.

Lennox discloses an endoprosthetic wrist joint wherein the radial component includes a part-annular, spherically shaped socket and the carpal component includes a spherical ball with flatted sides to allow free entry into the radial socket. The carpal component further includes an elongated member which is slotted to receive a plurality of metacarpal components, each including a spherical ball slid into the slot.

Frey discloses a three-component endoprosthetic wrist joint which includes an intermediate component member which interfaces with the proximal component by a ball and socket arrangement and with the distal component by means of a V-shaped recess and corresponding protruding portion. Movement is only permitted in one plane, but at two different locations along the longitudinal axis of the joint, and the V-shaped recess can be asymmetrical of its center plane so that a greater degree of pivoting can occur in one direction rather than in the opposite direction.

Laure discloses a wrist joint prosthesis which permits vertical motion and sidewise motion but prevents twisting motion around the longitudinal axis of the forearm. The prosthesis includes a ball and socket arrangement wherein an intermediate member serves as the socket for the distal component and as the ball for the proximal component and each ball and socket combination includes a slot and an outwardly protruding portion to restrict movement in only one plane.

Loda discloses a wrist joint prosthesis formed by a ball and socket joint, from which stems are introduced into at least one of the metacarpal bones and the radial bone, opposite to each other. In one version, the distal stem portion also provides a secondary stem which is nailable into another of the metacarpal bones. The prosthesis does not prevent the free rotation of the distal stem portion.

White discloses an endoprosthetic wrist joint providing a universal pivot between the radial component and the metacarpal component. An object is to provide a joint of greater strength which is therefore not dislocatable under an overload stress.

Hamas discloses a endoprosthetic wrist joint with a single spherical pivot providing unlimited motion in all directions as well as rotation. Certain preferred offsets and ratios are also disclosed.

In view of those desirable features previously discussed and the absence of such features by the disclosures of these listed patents, it would be an improvement to the devices of such patents and to prosthetic wrist joints in general to provide a prosthetic wrist joint of a design which permits a full range of motion, has torque relief for a calculated amount of rotation, has a biomechanically accurate center of rotation and is able to dislocate when loaded beyond capacity rather than to break or loosen. The prosthetic wrist joint described herein provides each of these desirable features as well as other improvements as will be apparent.

SUMMARY OF THE INVENTION

A prosthetic wrist joint according to one embodiment of the present invention comprises a radial component having a part-cylindrical bearing surface and means for anchoring into the end of the radius, a metacarpal component having a ball-like hinge member adjacent one end and means for anchoring into metacarpals adjacent the other end, an intermediate component positioned between the radial component and the metacarpal component and having a part-cylindrical bearing surface cooperatively engaging the bearing surface of the radial component for solely flexion and extension hinged motion and further having a socket-like recess receiving the ball-like hinge member for movement in the direction of radial-ulnar deviation, the socket-like recess being suitably sized and arranged relative to the ball-like hinge member so as to permit limited rotational movement of the metacarpal component relative to the radial component, about an axis substantially parallel with the longitudinal axis of the forearm, the angular rotational movement between extremes being less than thirty degrees.

One object of the present invention is to provide an improved prosthetic wrist joint.

Related objects and advantages of the present invention will be apparent from the following description.

DESCRIPTION OF THE PREFERRED EMBODIMENT

Figure 1:
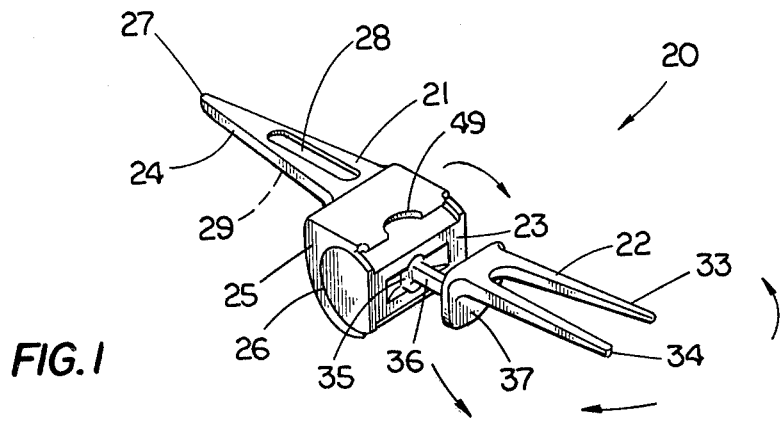
FIG. 1 is a perspective view of a prosthetic wrist joint according to a typical embodiment of the present invention.
Figure 2:
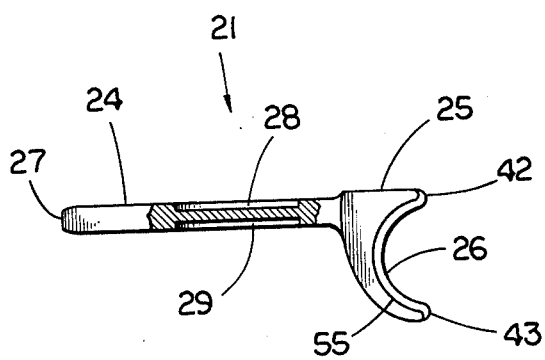
FIG. 2 is a side elevation view of a radial component comprising a portion of the FIG. 1 prosthetic wrist joint.
Figure 3:
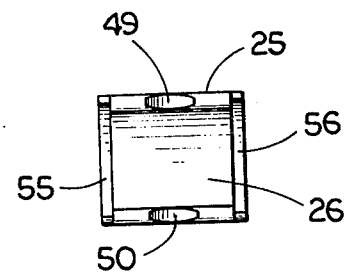
FIG. 3 is a front elevation view of the FIG. 2 radial component.
Figure 4:
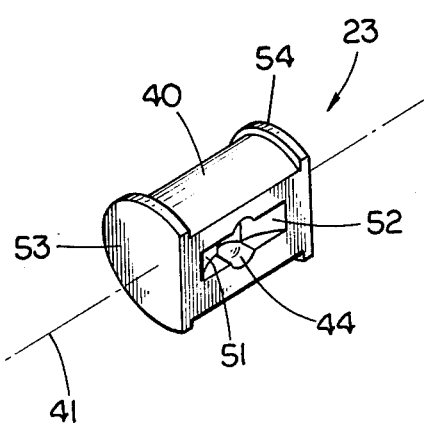
FIG. 4 is a perspective view of an intermediate component comprising a portion of the FIG. 1 prosthetic wrist joint.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated a prosthetic wrist joint 20 which includes a radial component 21, a metacarpal component 22 and an intermediate component 23 which is located between the radial component and the metacarpal component. The radial component 21 includes a stem portion 24 at one end and a head portion 25 at the opposite end. Head portion 25 includes a less-than-cylindrical bearing surface 26 and the entire radial component is a single integral piece constructed of a rigid, biologically inert metal, for example, stainless steel. Stem portion 24 is substantially flat and joins head portion 25 adjacent its uppermost surface. From this location of joining to head portion 25, stem portion 24 tapers to a point at end 27. Recesses 28 and 29 are disposed upon opposite surfaces of stem portion 24 and provide means to facilitate the anchoring of stem portion 24 into the end of the radius bone. Once the radius bone has been prepared for the insertion of radial component 21, stem portion 24 is inserted full length until head portion 25 contacts the end of the bone. Radial component 21 is fixed to the radius by the use of a suitable polymerizing grouting material such as methyl methacrylate. This material fills the various voids which might be present between the interior of the radius and stem portion 24 and then the material hardens to rigidly bond the radial component in place.

Figure 5:
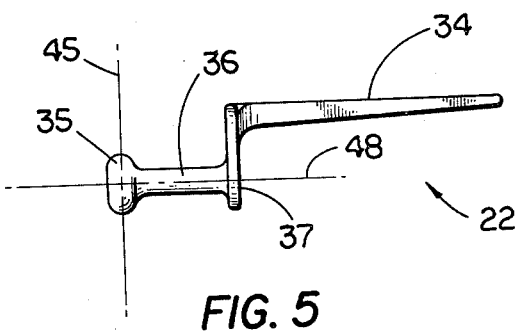
FIG. 5 is a side elevation view of a metacarpal component comprising a portion of the FIG. 1 prosthetic wrist joint.
Figure 6:
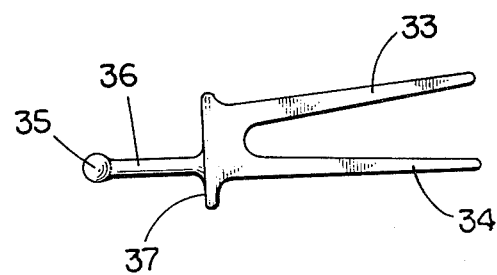
FIG. 6 is a plan view of the FIG. 5 metacarpal component.

The metacarpal component 22 (see FIGS. 5 and 6) includes a pair of outwardly protruding prong members 33 and 34 at one end and at the opposite end a ball-like hinge member 35 which is integral with prongs 33 and 34 by means of shaft 36 and plate 37. Ball-like hinge member 35 is of a modified geometry such that it is oblong yet ball-like on each end. The longitudinal axis of prong 34 and the longitudinal axis of shaft 36 are substantially parallel to each other and arranged so as to lie within a common vertical plane. Prong 33 is set at a slight angle relative to prong 34 such that prong 33 is suitable sized, arranged and spaced so as to be insertable into the second metacarpal while prong 34 is inserted into the third metacarpal. Once the second and third metacarpals are suitably prepared for the insertion of prongs 33 and 34, these prongs may be anchored in place by means of a material such as methyl methacrylate as has been previously mentioned for stem portion 24. Metacarpal component 22 is similarly constructed of a rigid, biologically inert metal such as, for example, stainless steel. Plate 37 is provided as a stop means to the continued insertion of prongs 33 and 34 such that plate 37 abuts the end of the second and third metacarpals once prongs 33 and 34 have achieved full insertion into their respective bones.

Figure 7:
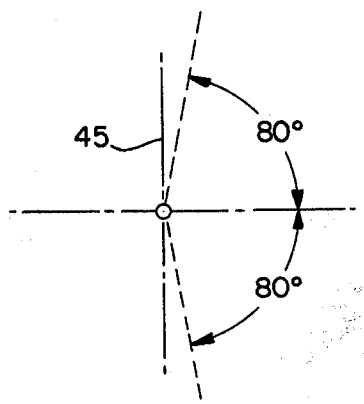
FIG. 7 is a diagrammatic illustration of the range of pivotal movement in the flexion-extention plane between the FIG. 5 metacarpal component and the FIG. 2 radial component.
Figure 8:
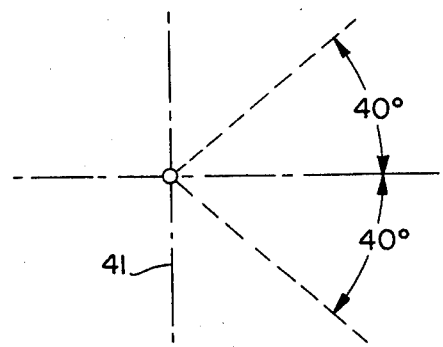
FIG. 8 is a diagrammatic illustration of the extent of movement permitted in the radial-ulnar deviation plane between the FIG. 5 metacarpal component and the FIG. 2 radial component.

Prosthetic wrist joint 20 achieves relative movement between the radial component 21 and the metacarpal component 22 by means of intermediate component 23. Intermediate component 23 is arranged with a less-than-cylindrical bearing surface 40 which is compatibly sized with bearing surface 40 which is compatibly sized with bearing surface 26 for sliding hinged movement about axis line 41 which is the center of the constant circular curvature of both bearing surface 40 as well as bearing surface 26. Both bearing surfaces 26 and 40 are less than cylindrical and this means that the angle of actual curvature is less than 360 degrees. As is illustrated, the constant curvature of bearing surface 26 extends for nearly 180 degrees while the constant curvature of bearing surface extends for approximately 240 degrees. Consequently, when bearing surface 40 is placed in contiguous abutting engagement with bearing surface 26 in a nonflexed orientation, a portion of bearing surface 40 extends beyond upper edge 42 as well as beyond lower edge 43 of head portion 25. This enables full bearing contact against surface 26 during moderate flexion and extension movements, and although the extremes of such movement are illustrated by FIG. 7; under normal ranges of movement, a significant majority of bearing surface 26 will be in contact with bearing surface 40. The flatted surface of intermediate component 23 includes a socket-like recess 44 which is arranged to receive and retain ball-like hinge member 35. Once hinge member is snapped into recess 44, metacarpal component 22 is able to pivot around axis line 45 with respect to intermediate component 23. This direction of pivotal movement corresponds to movement in the radial-ulnar deviation plane and the range of motion is illustrated by FIG. 8. Intermediate component 23 is constructed of a biologically inert plastic material which is self-lubricating with respect to the biologically inert metals used for radial component 21 and metacarpal component 22.

With virtually any prosthetic wrist joint device, what is desired is to provide a means to restore normal movement to the wrist such that the human being involved is able to utilize his hand and arm in a normal manner. The primary directions of movement of the wrist joint involve flexion and extension which is illustrated by FIG. 7 and is achieved by the hinged movement of bearing surface 26 with respect to bearing surface 40. There is no other motion permitted at this particular interface and consequently, the design of the engaging surfaces is uncomplicated. The second primary direction of motion is in the plane of radial-ulnar deviation and this is illustrated by FIG. 8 and is provided for by means of hinge member 35 and socket-like recess 44. This plane of radial-ulnar deviation movement is perpendicular to the plane of flexion and extension movement and axis line 41 intersects axis line 45 at a common point whose location is internal to intermediate component 23. There is still a further direction of movement associated with a wrist joint and this movement is rotational movement about an axis which is coincident with the longitudinal axis of the radius. Movement such as turning a doorknob requires that the hand be able to twist with the radius and although the hand and radius move together, there is still significant stress loading on the wrist joint and any suitable prosthetic device must be capable of accepting such loads without breaking or loosening. In order to assure that the hand rotates with the radius, most prosthetic wrist joints are constructed so that no rotational movement about the longitudinal axis of the arm is permitted. However, although prosthetic wrist joint 20, as has been described, has two primary planes of pivotal motion, one about axis line 41 and the other about axis line 45, prosthetic wrist joint 20 is arranged in such a manner as to permit a limited rotational movement of metacarpal component 22 with respect to radial component 21. This limited rotational movement is provided by means of the size and arrangement of ball-like hinge member 35 and socket-like recess 44. Although these two component pieces are not permitted to move within the flexion and extension planes, their respective geometries and curvatures do allow a slight twisting action of the ball-like hinge member 35 within the socket-like recess 44 such that the metacarpal component 22 is able to rotate to a limited extent with respect to radial component 21 about axis line 48 which is substantially parallel with the longitudinal axis of the forearm. This limited rotational movement is restricted to fifteen degrees in a clockwise direction and fifteen degrees in a counterclockwise direction such that the total angular movement is limited to a maximum travel of about thirty degrees between extremes. Axis line 48 is positioned such that axis lines 41, 45 and 48 all have a single point in common which is interior to intermediate component 23.

In those devices which do not permit any rotational movement whatsoever, repeated twisting and rotation can ultimately result in a failure of bone, prosthesis, cement or the intermediate component which may be, for example, constructed of polyethylene. It is hoped that such a failure would be in a component such as the replaceable polyethylene component, however, repeated rotational motions may in fact fatigue the cement-to-bone interface and ultimately lead to prosthesis loosening. Therefore, the calculated amount of rotation (maximum of 30 degrees) has been built into prosthetic wrist joint 20 in order to allow for small rotational displacements of the metacarpals with respect to the radius. This small rotational displacement obviates stress being absorbed by one of the structural components of the prosthesis.

One design constraint of any prosthetic wrist joint is that the distance from the end of the radius to the end of the metacarpals into which the prosthesis is inserted is typically of a fixed overall dimension and although the ends of these respective bones may be surgically modified as part of the implant procedure, the overall length is still a consideration. A further design constraint is the overall thickness of the prosthetic wrist joint in that the human hand is somewhat flat at that point and the surrounding bones and soft tissue must be able to fit in and around the prosthesis in order to result in a wrist which externally appears to be normal. It would not be suitable for the wrist to have large bulges or surface disruptions caused by a prosthetic device which was poorly or improperly sized or too large to be accommodated by the wrist. Although many prosthetic wrist joints provide a bearing surface of a generally spherical form, this is not advantageous due to the fact that a sphere has the same dimension in all directions and consequently in order to get a larger bearing surface area, the dimensions of the prosthesis must be increased in all directions. This may result in a prosthetic wrist joint which is too large for the surrounding bones and soft tissue.

Therefore, the size of the spherical bearing surface must be reduced in order to fit and when this size reduction is made, the load per unit area on the bearing surface must naturally increase. Prosthetic wrist joint 20 disclosed herein overcomes this disadvantage by providing a generally cylindrical bearing surface having a length dimension which is larger than its diameter. Although a cylindrical bearing surface having the same length as diameter provides no greater surface area over that of a sphere, a cylindrical bearing surface may be increased in length without increasing the diameter measurement and thereby provide a larger bearing surface area without causing the prosthetic wrist joint to grow in thickness. This allows the prosthesis to remain comfortably disposed within the wrist area. A further difference between a spherical bearing surface and the disclosed cylindrical bearing surface is the direction of forces and force vectors. A cylindrical bearing surface whose length is greater than its diameter as disclosed herein provides a greater surface area in a direction normal to the forces tending to compress the intermediate component into the radial component and thus with more surface area, there is a lower contact stress.

Although relative degrees of pivotal movement have been illustrated by FIGS. 7 and 8, these angular values are not limiting but rather refer to extremes which are permitted by prosthetic wrist joint 20 under normal circumstances. The flexion and extension range of 80 degrees up as well as 80 degrees down is limited by the contact of shaft 36 with circular notch 49 on the top of radial component 21 and circular notch 50 on the bottom. Similarly, the 40 degrees to the left and 40 degrees to the right motion permitted between hinge member 35 and socket-like recess 44 is limited by the engagement of shaft 36 with tapered side portion 51 on one side and by shaft 36 with tapered side portion 52 on the opposite side of socket-like recess 44. However, neither of these motion-limiting aspects of prosthetic wrist joint 20 either in the plane of flexion and extension or in the plane of radial-ulnar deviation are limiting to the extent that the prosthetic components are stressed when the movement exceeds either the 80 degree or the 40 degree ranges. For example, if the user of the prosthetic wrist joint would fall on the wrist, the indicated 80 degree movement might be extended to 90 degrees or more. If circular notches 49 and 50 were in fact limiting structural features, then radial component 21 as well as shaft 36 would be stress-loaded by this additional 10 degrees or more of flexion movement. However, what occurs with prosthetic wrist joint 20 is that intermediate component 23 will slide out of contact with radial component 21 at their corresponding bearing surfaces thereby preventing any stress loading on the prosthetic components and allowing the wrist to absorb this additional flexion movement without permanent injury or prosthetic damage. Consequently, the physician may relocate the intermediate component back into engagement with the bearing surface of radial component 21 and this relocation by closed reduction spares the patient the significant pain involved with the reoperating in order to repair a broken or loosened prosthesis. Similarly, in the plane of radial-ulnar deviation when the prosthetic wrist joint is loaded beyond the capacity, the intermediate component 23 will dislocate out of engagement with bearing surface 26 rather than break or loosen. Similarly, intermediate component 23 may again be relocated by closed reduction. This concept of the intermediate component being able to dislocate from radial component 21 is referred to as motion relief wherein a full range of motion in both the flexion and extension planes as well as in the radial-ulnar deviation plane is permitted and wrist motion is limited solely by the surrounding soft tissue of the anatomy of the arm and hand rather than by the wrist prosthesis itself. As pointed out, the benefit from this full range of motion and motion relief is that the prosthesis is not subject to repeated stresses than can cause breakage or loosening.

Figure 9:
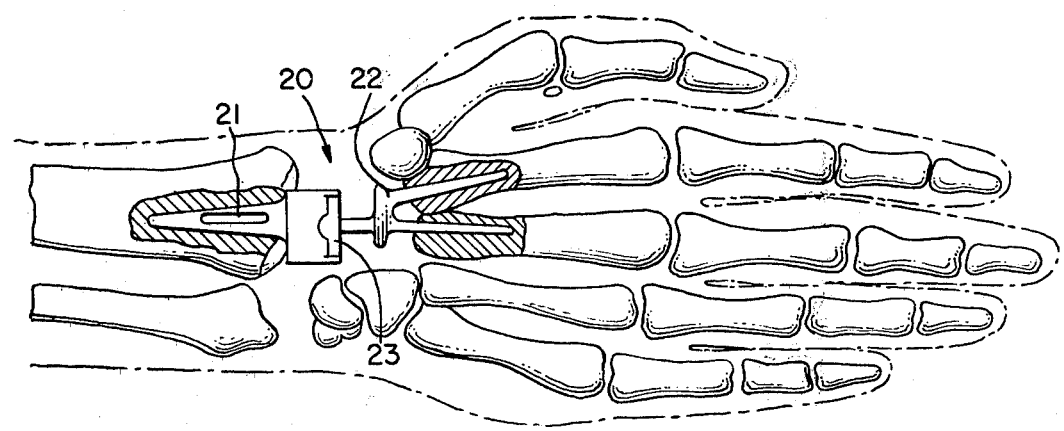
FIG. 9 is diagrammatic, plan view of the FIG. 1 prosthetic wrist joint as inserted into the radius and metacarpals of a human's anatomy.

In order to allow this motion relief and dislocating aspect, it is important that bearing surfaces 26 and 40 engage each other such that surface 40 is free to separate from surface 26. This requires that the angular inclusion of bearing surface 26 be 180° or somewhat less. Although an angular measurement slightly greater than 180° could be accommodated by requiring that intermediate component 23 snap out of radial component 21, it is preferred to allow bearing surface 40 to freely separate from bearing surface 26 when the prosthetic wrist joint is loaded beyond capacity in one of the two pivotal motion planes. By providing bearing surface 26 of an angular measurement of 180° or less there is then a concern of retaining intermediate component 23 in such a way that movement in undesired directions is prevented. Consequently, in order to prevent subluxing in the medial-lateral plane, intermediate component 23 is provided with a pair of oppositely disposed, part-circular end flanges 53 and 54. Similarly, the head portion 25 of radial component 21 is provided with a pair of shoulder portions 55 and 56 which are disposed on opposite ends of bearing surface 26. Shoulder portions 55 and 56 are compatibly sized and arranged to receive end flanges 53 and 54 such that lateral movement between intermediate component 23 and radial component 21 is prevented. This assures that the only motion occurring between intermediate component 23 and radial component 21 is pivotal motion about axis line 41 as has been previously disclosed. A further feature of prosthetic wrist joint 20 is that the wrist prosthesis has a center of rotation that is anatomically centered rather than being centered about the stem axis of the prosthesis itself. Studies have shown that the anatomical center of rotation in the wrist is in the head of the capitate (ulnarward) and displaced slightly volarward. Using a prosthesis with an anatomical center is important in that it allows restoration of an arthritic hand to its normal position. Patients with severe metacarpal-radial arthritis have hands which are pulled ulnarward and volarward. The reason for the arthritic deformity is that the deteriorated wrist has reduced the leverage of the dorsal and radial muscles in the hand. By using the prosthetic wrist joint disclosed herein having an anatomical center, the dorsal and radial muscles regain their correct positioning and leverage and draw the hand back into a normal position. As has been previously mentioned, the longitudinal axis of prong 34 is substantially parallel to the longitudinal axis of shaft 36 and inasmuch as the longitudinal axis of shaft 36 is coincident with axis line 48 which is the axis of the limited rotational movement, it can be seen from FIG. 9 that insertion of prong 34 into the third metacarpal of the hand results in positioning the axis of rotation (axis line 48) at the anatomical center of rotation of the wrist. It should also be pointed out that the longitudinal axis of shaft 36 and prong 34 do not coincide with the longitudinal axis of stem portion 24. It is also important that this anatomical center of rotation be achieved by the structure of the prosthetic wrist joint and not be means of a forced modification at the time of insertion. For example, if this anatomical center of rotation was attempted to be achieved by bending the stems of the radial component, this could cause possible damage to the prosthesis during insertion and would thus be unacceptable.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A prosthetic wrist joint comprising:
   a radial component having a part-cylindrical bearing surface and means for anchoring into the end of a radius bone;
   a metacarpal component having a ball-like hinge member adjacent one end and means adjacent the other end for anchoring into metacarpals; and
   an intermediate component positioned between said radial component and said metacarpal component and having a part-cylindrical bearing surface cooperatively engaging the bearing surface of said radial component for solely flexion and extension hinged movement and a socket-like recess receiving said ball-like hinge member for movement in the direction of radial-ulnar deviation, said socket-like recess being suitably sized and arranged relative to said ball-like hinge member so as to permit limited rotational movement of said metacarpal component relative to said radial component about an axis substantially parallel with the longitudinal axis of the forearm, the angular rotational movement between extremes being less than 30 degrees, in which said intermediate component further includes a pair of oppositely disposed, part-circular end flanges and said radial component having a corresponding pair of oppositely disposed shoulder portions adjacent said bearing surface, said end flanges being received by said shoulder portions for preventing the prosthetic wrist joint from subluxing in the medial-lateral plane.

2. The prosthetic wrist joint of claim 1 wherein the length of the part-cylindrical bearing surface of said intermediate component being greater than the diameter of said same bearing surface.

3. The prosthetic wrist joint of claim 2 wherein the axis of said limited rotational movement being in a plane coextensive with the anatomical center of rotation in the wrist.

4. The prosthetic wrist joint of claim 3 wherein said radial component and said metacarpal component are arranged with respect to said intermediate component so as to be free of any means to restrict relative movement therebetween, said relative movement being limited solely by the soft tissue of the anatomy surrounding said prosthetic wrist joint.

5. The prosthetic wrist joint of claim 4 wherein said radial component and said metacarpal component are constructed of a rigid, biologically inert metal and said intermediate component is constructed of a biologically inert plastic material which is self-lubricating with respect to said biologically inert metal.

6. The prosthetic wrist joint of claim 5 wherein the means for anchoring of said metacarpal component includes a first prong portion for insertion into the second metacarpal and a second prong portion for insertion into the third metacarpal.

7. A prosthetic wrist joint comprising;
   a radial component having a part-cylindrical bearing surface and means for anchoring into the end of a radius bone;
   a metacarpal component having a ball-like hinge member adjacent one end and means adjacent the other end for anchoring into metacarpals; and
   an intermediate component positioned between said radial component and said metacarpal component and having a part-cylindrical bearing surface disposed contiguous to the part-cylindrical bearing surface of said radial component for hinged movement solely in a first plane, said intermediate component further having a socket-like recess arranged for receiving and retaining said ball-like hinge member for pivotal movement in a second plane and for a limited rotational movement about the longitudinal axis of the arm of said metacarpal component relative to said radial component, the axis of said limited rotational movement being in a plane coextensive with the anatomical center of rotation in the wrist, in which said intermediate component further includes a pair of oppositely disposed, part-circular end flanges and said radial component having a corresponding pair of oppositely disposed shoulder portions adjacent said bearing surface, said end flanges being received by said shoulder portions for preventing the prosthetic wrist joint from subluxing in the medial-lateral plane.

8. The prosthetic wrist joint of claim 7 wherein the length of the part-cylindrical bearing surface of said intermediate component being greater than the diameter of said same bearing surface.

9. The prosthetic wrist joint of claim 8 wherein said radial component and said metacarpal component are arranged with respect to said intermediate component so as to be free of any means to restrict motion in either of said two planes, said motion being limited solely by the soft tissue of the anatomy surrounding said prosthetic wrist joint.

10. The prosthetic wrist joint of claim 9 wherein said radial component and said metacarpal component are constructed of a rigid, biologically inert metal and said intermediate component is constructed of a biologically inert plastic material which is self-lubricating with respect to said biologically inert metal, and wherein the means for anchoring of said metacarpal component includes a first prong portion for insertion into the second metacarpal and a second prong portion for insertion into the third metacarpal.

11. The prosthetic wrist joint of claim 10 wherein the axis of the pivotal movement in said first plane, the axis of the pivotal movement in said second plane and the axis of said limited rotational movement each having a single point in common, said common point being interior to said intermediate component.

12. A prosthetic wrist joint for anchoring into a human's radius bone and into at least one metacarpal bone, said prosthetic wrist joint comprising:
   a radial component having a less-than-cylindrical constant curvature bearing surface;
   a metacarpal component having a modified, ball-like protruding portion; and
   an intermediate component positioned between said radial component and said metacarpal component and having a bearing surface abutting the constant curvature bearing surface of said radial component and a socket-like recess receiving said ball-like protruding portion, said intermediate component being suitably arranged for pivotal motion between said radial component and said metacarpal component in a first plane and for pivotal motion between said radial component and said metacarpal component in a second plane perpendicular to said first plane, said pivotal motions being independent of each other, said radial component and said metacarpal component being arranged with respect to said intermediate component so as to be free of any means to restrict said pivotal motions, said pivotal motions being limited solely by soft tissue of the anatomy surrounding said prosthetic wrist joint, in which said intermediate component further includes pair of oppositely disposed, part-circular end flanges and said radial component having a corresponding pair of oppositely disposed shoulder portions adjacent said bearing surface, said end flanges being received by said shoulder portions for preventing the prosthetic wrist joint from subluxing in the medial-lateral plane.

13. The prosthetic wrist joint of claim 12 wherein the length of the part-cylindrical bearing surface of said intermediate component being greater than the diameter of said same bearing surface.

14. The prosthetic wrist joint of claim 13 wherein said socket-like recess and said modified, ball-like protruding portion being suitably sized and arranged to permit limited rotational movement of said metacarpal component relative to said radial component about an axis substantially parallel to the longitudinal axis of the forearm, the angular rotational movement between extremes being less than 30 degrees.

15. The prosthetic wrist joint of claim 14 wherein the axis of said limited rotational movement being in a plane coextensive with the anatomical center of rotation in the wrist.

16. The prosthetic wrist joint of claim 15 wherein said radial component and said metacarpal component are constructed of a rigid, biologically inert metal and said intermediate component is constructed of a biologically inert plastic material which is self-lubricating with respect to said biologically inert metal, and wherein the means for anchoring of said metacarpal component includes a first prong portion for insertion into the second metacarpal and a second prong portion for insertion into the third metacarpal.

* * * * *